United States Patent
Casteel et al.

(10) Patent No.: US 9,340,568 B2
(45) Date of Patent: May 17, 2016

(54) SOLID FORMS OF AN ANTIVIRAL COMPOUND

(71) Applicant: Gilead Pharmasset LLC, Foster City, CA (US)

(72) Inventors: Melissa Jean Casteel, Foster City, CA (US); Kathleen Dashner, Foster City, CA (US); Hyuk-Jun Jung, Shiheung-si (KR); Mun Sik Seo, Shiheung-si (KR); Bing Shi, Redwood City, CA (US); Fang Wang, Foster City, CA (US); Vahid Zia, Foster City, CA (US)

(73) Assignee: GILEAD PHARMASSET LLC, Foster City, CA (US)

( * ) Notice: Subject to any disclaimer, the term of this patent is extended or adjusted under 35 U.S.C. 154(b) by 0 days.

(21) Appl. No.: 14/563,639

(22) Filed: Dec. 8, 2014

(65) Prior Publication Data
US 2015/0175646 A1   Jun. 25, 2015

Related U.S. Application Data

(60) Provisional application No. 61/920,371, filed on Dec. 23, 2013.

(51) Int. Cl.
| | | |
|---|---|---|
| A01N 43/04 | (2006.01) | |
| A61K 31/70 | (2006.01) | |
| C07H 19/10 | (2006.01) | |
| A61K 31/7052 | (2006.01) | |
| A61K 31/7064 | (2006.01) | |
| A61K 31/706 | (2006.01) | |
| A61K 31/7068 | (2006.01) | |
| A61K 31/7072 | (2006.01) | |
| C07F 9/6558 | (2006.01) | |
| C07H 19/06 | (2006.01) | |

(52) U.S. Cl.
CPC ............. *C07H 19/10* (2013.01); *A61K 31/706* (2013.01); *A61K 31/7052* (2013.01); *A61K 31/7064* (2013.01); *A61K 31/7068* (2013.01); *A61K 31/7072* (2013.01); *C07F 9/65586* (2013.01); *C07H 19/06* (2013.01)

(58) Field of Classification Search
None
See application file for complete search history.

(56) References Cited

U.S. PATENT DOCUMENTS

| | | | |
|---|---|---|---|
| 7,964,580 B2 | 6/2011 | Sofia et al. | |
| 8,618,076 B2 | 12/2013 | Ross et al. | |
| 8,642,756 B2 * | 2/2014 | Ross | C07H 19/10 536/117 |

OTHER PUBLICATIONS

Int'l Search Report—Writte Opinion Dated Jul. 2, 2015 For PCT/US2014/069123.

* cited by examiner

*Primary Examiner* — Patrick Lewis

(57) ABSTRACT

Crystalline solid forms of the anti-HCV compound (S)-isopropyl 2-((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphorylamino)propanoate (Compound I) are described (Compound I)

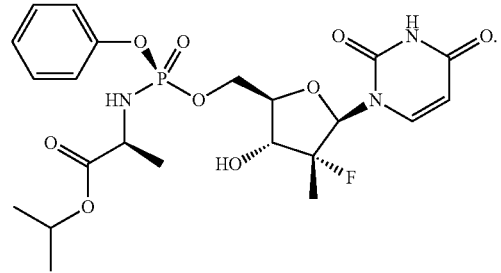

Also provided are processes of making and methods of using the crystalline forms.

10 Claims, 10 Drawing Sheets

SOLID FORMS OF AN ANTIVIRAL COMPOUND

CROSS REFERENCE

This application claims the benefits of U.S. Provisional Application No. 61/920,371, filed on Dec. 23, 2013, the entire disclosure of which is incorporated herein by reference.

BACKGROUND

Hepatitis C is recognized as a chronic viral disease of the liver. Although drugs targeting the liver are in wide use and have shown efficacy, toxicity and other side effects have limited their usefulness. Inhibitors of hepatitis C virus (HCV) are useful to limit the establishment and progression of infection by HCV as well as in diagnostic assays for HCV.

The compound (S)-isopropyl 2-((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphorylamino)propanoate, designated herein as Compound I, also known as Sofosbuvir, is an effective anti-HCV agent and is described in International Publication Numbers WO 2008/121634 and WO 2011/123654, and in U.S. Pat. Nos. 7,964,580 and 8,618,076. While certain crystalline forms of Compound I have been reported, Compound I was not heretofore known in the crystalline forms described herein.

SUMMARY

The present disclosure relates to crystalline solid forms of the compound (S)-isopropyl 2-((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphorylamino)propanoate (Compound I)

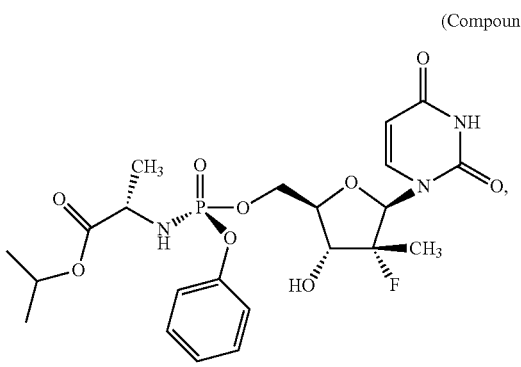

(Compound I)

processes for making the crystalline solid forms of Compound I, and their therapeutic methods of use.

The present disclosure provides two crystalline forms of Compound I, referred to herein as Form 7 and Form 8. Forms 7 and 8 may be characterized and distinguished from other solid forms of the same compound using various analytical techniques including, but not limited to, X-ray powder diffraction (XRPD), solid-state nuclear magnetic resonance (NMR, or $^{13}C$ SSNMR), Raman spectroscopy, differential scanning calorimetry (DSC), dynamic vapor sorption (DVS), and thermogravimetric analysis (TGA). The disclosure also provides processes for making the crystalline forms and methods for using them in the treatment of HCV.

One embodiment is a crystalline form of (S)-isopropyl 2-((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphorylamino) propanoate (Compound I) characterized by an XRPD diffractogram comprising at least two peaks chosen from the following list: 12.6, 13.5, 16.9, and 17.3 degrees two-theta (°2θ), ±0.2° 2θ. Another embodiment is crystalline Compound I characterized by an XRPD diffractogram comprising peaks at 12.6 and 13.5 °2θ±0.2° 2θ. Another embodiment is crystalline Compound I characterized by an XRPD diffractogram comprising peaks at 12.6, 13.5, and 17.3 °2θ±0.2° 2θ. Another embodiment is crystalline Compound I characterized by an XRPD diffractogram comprising peaks at 12.6, 13.5, 16.9, and 17.3 °2θ±0.2° 2θ. These crystalline forms of Compound I are referred to as Compound I, Form 7.

Another embodiment is a crystalline form of Compound I characterized by an XRPD diffractogram comprising at least two peaks chosen from the following list: 8.6, 9.2, 14.2, 15.6, 16.0, 17.1, 17.5, 18.1, 19.8, and 25.6 °2θ±0.2° 2θ. Another embodiment is crystalline Compound I characterized by an XRPD spectrum comprising peaks at 8.6, 9.2 and 17.1 °2θ±0.2° 2θ. These crystalline forms of Compound I are referred to as Compound I, Form 8.

In another embodiment, provided herein is a method of treating a human subject infected with hepatitis C virus comprising administering to the human subject a therapeutically effective amount of Compound I, Form 7 or Compound I, Form 8. In another embodiment, provided herein is a method of treating a human subject infected with hepatitis C virus comprising administering to the human subject a pharmaceutical composition comprising a therapeutically effective amount of Compound I, Form 7 or Compound I, Form 8 and a pharmaceutically acceptable excipient.

Another embodiment is a pharmaceutical composition comprising Compound I, Form 7 or Compound I, Form 8 and a pharmaceutically acceptable excipient.

In still a further embodiment is a crystalline compound as defined herein or a pharmaceutical composition comprising the same for the treatment of a human subject infected by hepatitis C virus, use of the crystalline compound as defined herein or the pharmaceutical composition comprising the same for the treatment of a human subject infected by hepatitis C virus, use of the crystalline compound as defined herein or the pharmaceutical composition comprising the same for the manufacture of a medicament for the treatment of a human subject infected by hepatitis C virus, and use of a crystalline compound as defined herein or a pharmaceutical composition comprising the same in therapy.

DETAILED DESCRIPTION

Figure 1:
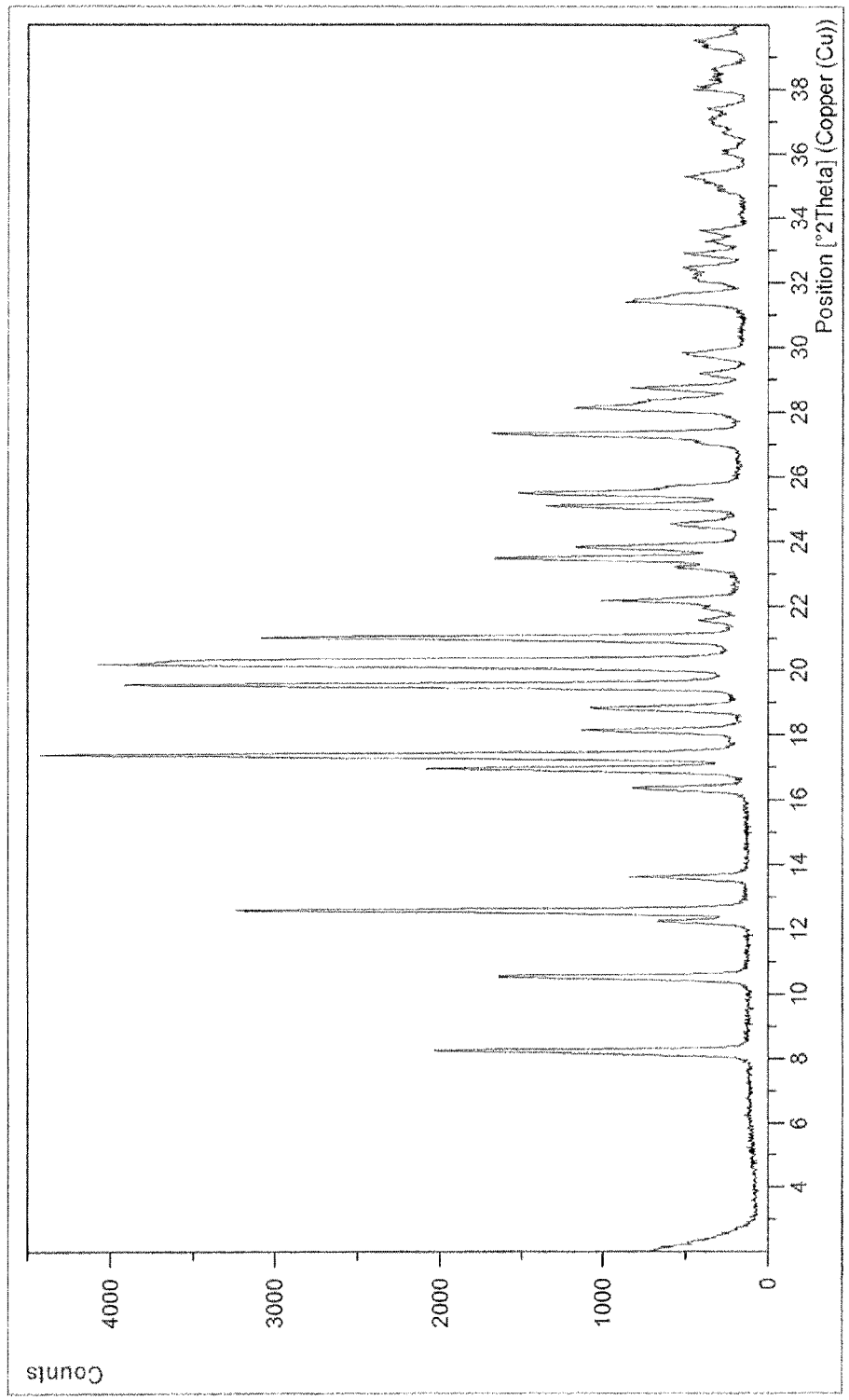
FIG. 1 is an XRPD diffractogram of Compound I, Form 7.

As used in the present specification, the following words and phrases are generally intended to have the meanings as set forth below, except to the extent that the context in which they are used indicates otherwise.

The term "therapeutically effective amount" refers to an amount that is sufficient to effect treatment, as defined below, when administered to a human in need of such treatment. The therapeutically effective amount will vary depending upon the human subject being treated, the weight and age of the human subject, the severity of the disease condition, the manner of administration and the like, which can readily be determined by one of ordinary skill in the art.

One embodiment is crystalline (S)-isopropyl 2-(((S)-(((2R,3R,4R,5R)-5-(2,4-dioxo-3,4-dihydropyrimidin-1 (2H)-yl)-4-fluoro-3-hydroxy-4-methyltetrahydrofuran-2-yl) methoxy)(phenoxy)phosphoryeamino) propanoate (Compound I, Form 7) characterized by an X-ray powder diffractogram comprising at least three peaks chosen from the following list: 8.2, 10.5, 12.6, 17.0, 17.3, 19.5, 20.2, 21.0, 23.4, and 27.3 degrees two-theta (°2θ)±0.2° 2θ. Another embodiment is crystalline Compound I, Form 7, characterized by an XRPD diffractogram comprising at least two peaks chosen from the following list: 12.6, 13.5, 16.9, and 17.3 °2θ±0.2° 2θ. Another embodiment is crystalline Compound I, Form 7, characterized by an XRPD diffractogram comprising peaks at 12.6 and 13.5 °2θ±0.2° 2θ. Another embodiment is crystalline Compound I, Form 7, characterized by an XRPD diffractogram comprising peaks at 12.6, 13.5, and 17.3 °2θ±0.2° 2θ. Another embodiment is crystalline Compound I, Form 7, characterized by an XRPD diffractogram comprising peaks at 12.6, 13.5, 16.9, and 17.3 °2θ±0.2° 2θ. Another embodiment is crystalline Compound I, Form 7, characterized by an XRPD diffractogram comprising at least three peaks chosen from the following list: 8.2, 10.5, 12.6, 13.5, 16.9, 17.0, 17.3, 19.5, 20.2, 21.0, 23.4, and 27.3 °2θ±0.2° 2θ. Another embodiment is crystalline Compound I, Form 7, characterized by an XRPD diffractogram comprising at least five peaks chosen from the following list: 8.2, 10.5, 12.6, 13.5, 16.9, 17.0, 17.3, 19.5, 20.2, 21.0, 23.4, and 27.3 °2θ±0.2° 2θ. Another embodiment is crystalline Compound I, Form 7, characterized by an XRPD diffractogram comprising the following peaks: 8.2, 10.5, 12.6, 13.5, 16.9, 17.0, 17.3, 19.5, 20.2, 21.0, 23.4, and 27.3 °2θ±0.2° 2θ.

Another embodiment is crystalline Compound I, Form 7, characterized by an XRPD diffractogram comprising at least three d-spacing values from the following list: 10.8, 8.4, 7.1, 6.6, 5.2, 5.1, 4.6, 4.4, 4.2, 3.8 and 3.3 angstroms (Å). In another embodiment, the crystalline Compound I, Form 7 is characterized by at least two of the following d-spacing values: 7.1, 6.6, 5.2, 5.1 angstroms (Å). In a further embodiment, the crystalline Compound, Form 7 is characterized by d-spacing values at 7.1 and 6.6 angstroms (Å). Another embodiment is crystalline Compound I, Form 7, characterized by an XRPD diffractogram comprising d-spacing values at 7.1, 6.6, and 5.1 angstroms (Å). Another embodiment is crystalline Compound I, Form 7, characterized by an XRPD diffractogram comprising d-spacing values at 7.1, 6.6, 5.2, and 5.1 angstroms (Å). Another embodiment is crystalline Compound I, Form 7, characterized by an XRPD diffractogram comprising at least five d-spacing values from the following list: 10.8, 8.4, 7.1, 6.6, 5.2, 5.1, 4.6, 4.4, 4.2, 3.8 and 3.3 angstroms (Å). The relationship between peak positions and d-spacing values for Form 7 is found in Table 1 and the paragraph immediately following it.

Another embodiment is crystalline Compound I, Form 7, characterized by an XRPD diffractogram having peak positions (2θ values) substantially as listed for Form 7 in Table 1. Another embodiment is crystalline Compound I, Form 7, characterized by an XRPD diffractogram having d-spacing values substantially as listed for Form 7 in Table 1. Another embodiment is crystalline Compound I, Form 7, characterized by an XRPD diffractogram substantially as shown in FIG. 1.

Figure 2:
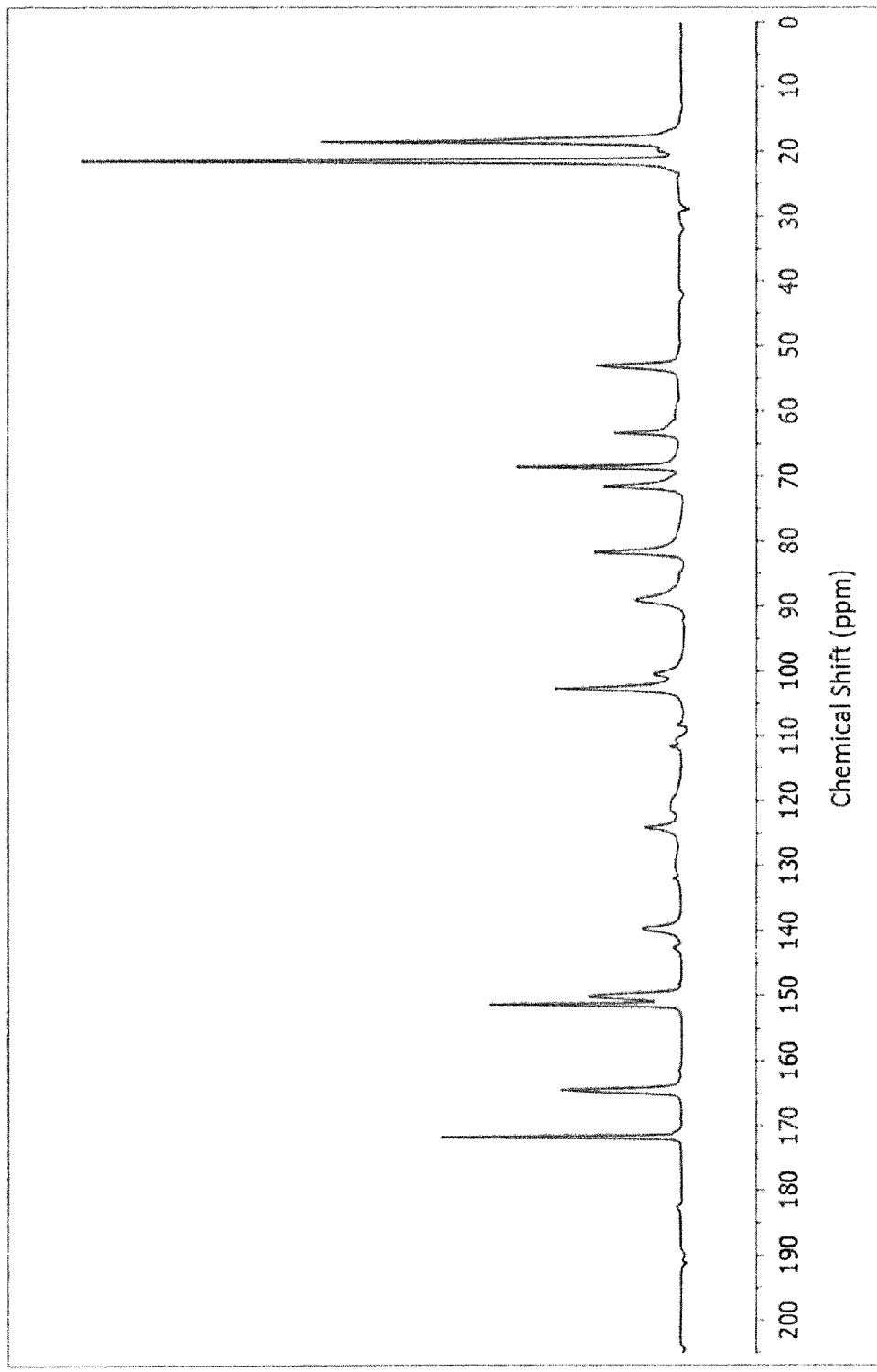
FIG. 2 is a $^{13}C$ SSNMR spectrum of Compound I, Form 7.

In another embodiment, Compound I, Form 7 is characterized by a $^{13}$C SSNMR spectrum comprising peaks at 18.6, 164.5, and 171.8 ppm. In another embodiment, the $^{13}$C SSNMR spectrum further comprises peaks at 21.5, 68.7, 81.7, 102.8, and 151.4 ppm. In another embodiment, Compound I, Form 7 is characterized by a $^{13}$C SSNMR spectrum substantially as shown in FIG. 2.

Figure 3:
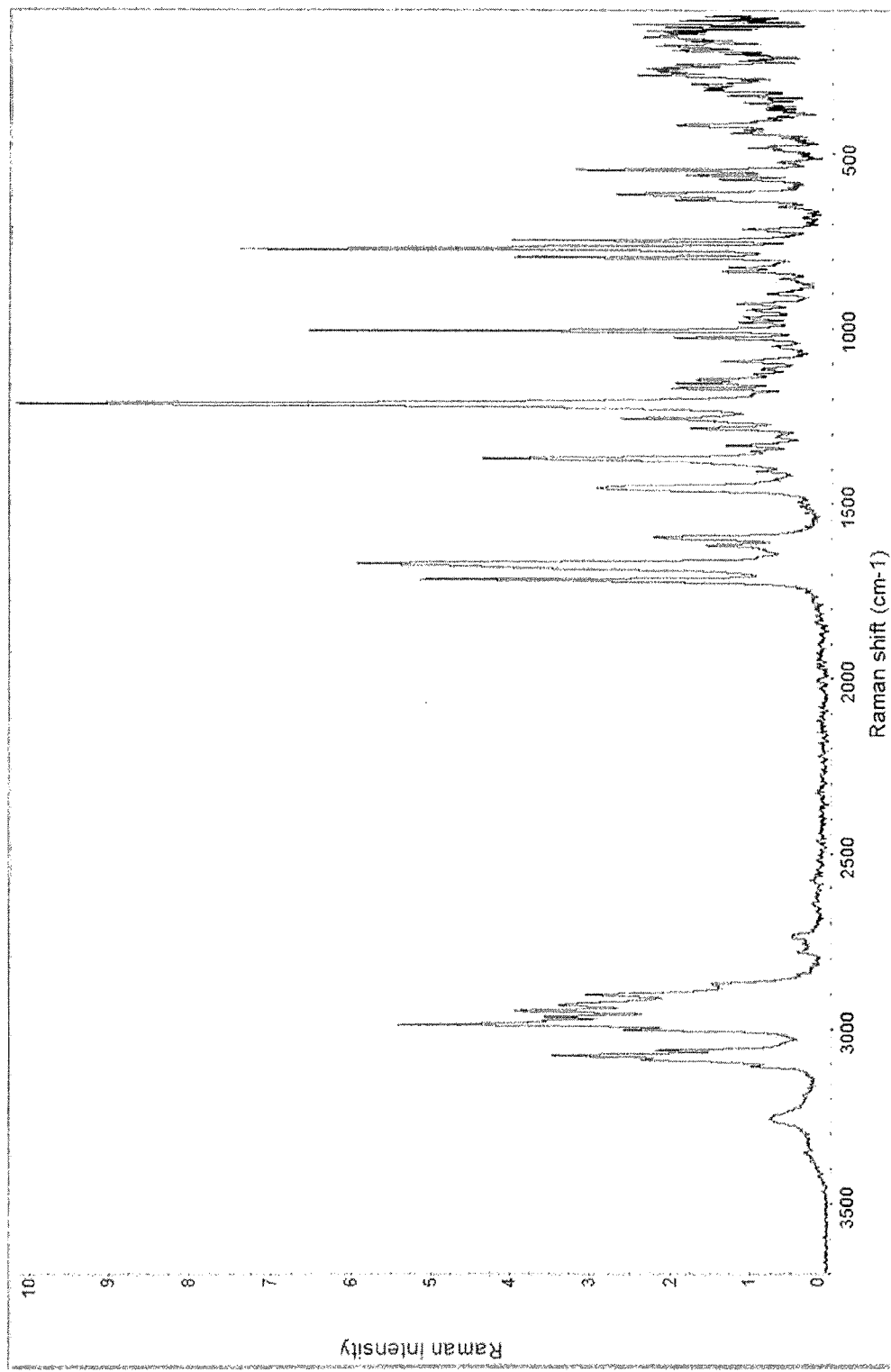
FIG. 3 is an FT-Raman spectrum of Compound I, Form 7.

In another embodiment, Compound I, Form 7 is characterized by an FT-Raman spectrum comprising peaks at 748, 774, 1006, 1216, and 1717 cm$^{-1}$. In another embodiment, the FT-Raman spectrum further comprises peaks at 545, 616, 1027, 1372, 2949, and 2988 cm$^{-1}$. In another embodiment, Compound I, Form 7 is characterized by an FT-Raman spectrum substantially as shown in FIG. 3.

Figure 4:
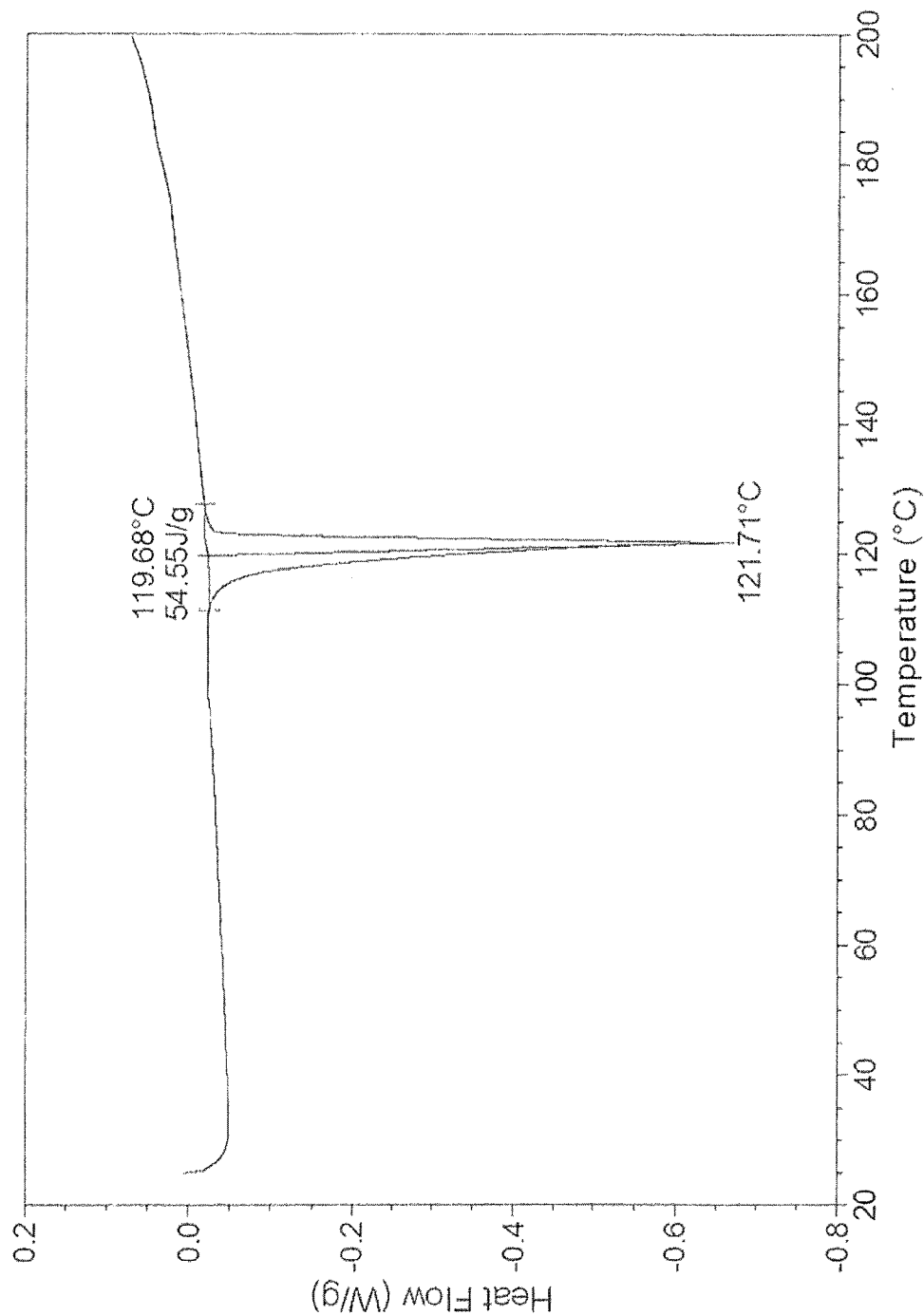
FIG. 4 is a DSC plot of Compound I, Form 7.

In another embodiment, Compound I, Form 7 is characterized by a differential scanning calorimetry (DSC) endotherm with an onset at 119-120° C. In another embodiment, Compound I, Form 7 is characterized by a DSC endotherm with a peak at about 122° C. In another embodiment, the DSC curve is substantially as shown in FIG. 4.

Figure 5:
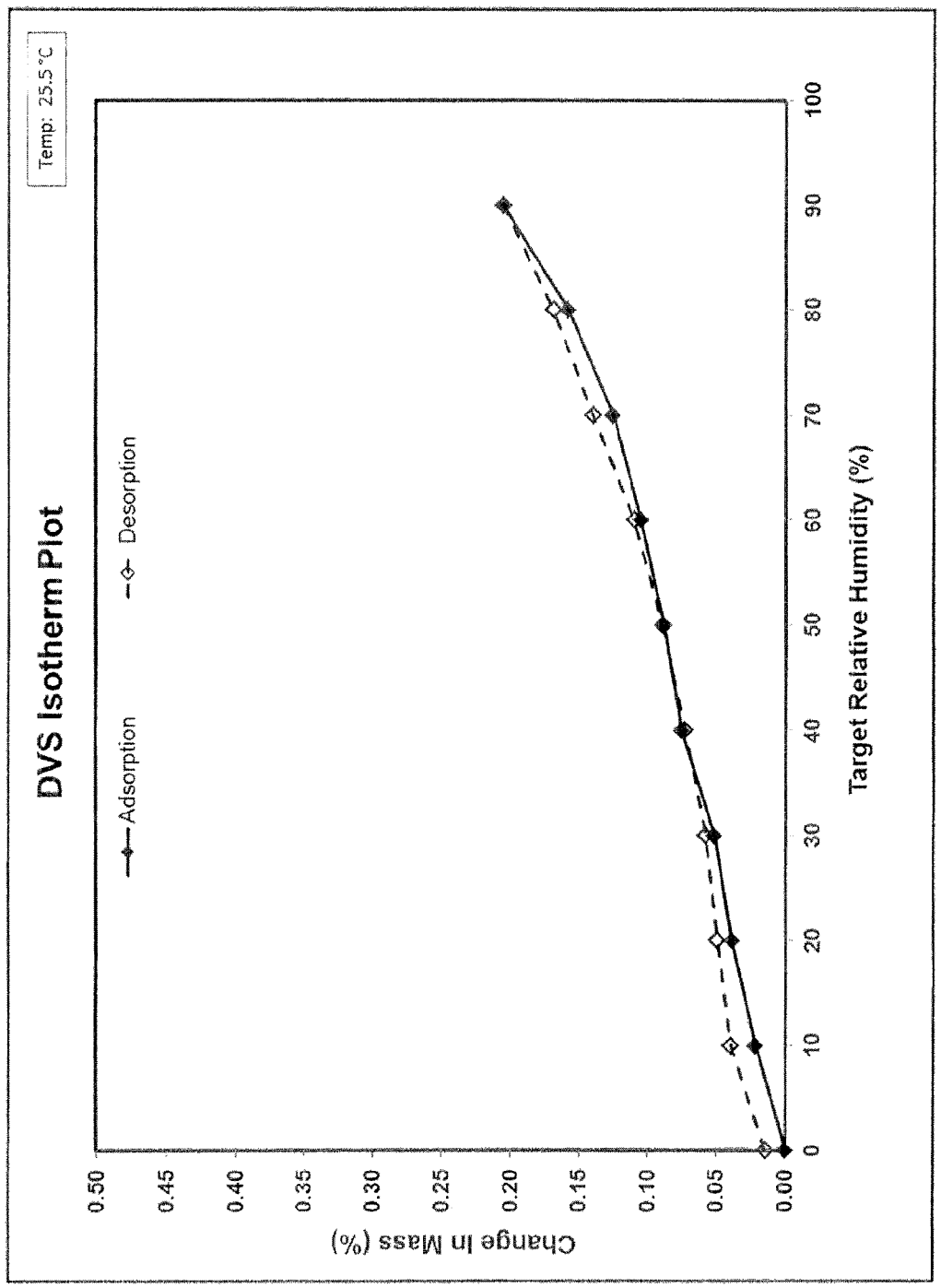
FIG. 5 is a DVS plot of Compound I, Form 7.

In another embodiment, Compound I, Form 7 is characterized by a change in mass of about 0.15% at a relative humidity (RH) of 90% (sorption cycle 1) as measured by dynamic vapor sorption (DVS). In another embodiment, the DVS is substantially as shown in FIG. 5.

In another embodiment, Compound I, Form 7 is characterized by at least two of the following:
an XRPD spectrum comprising peaks at 12.6 and 13.5 °2θ;
a $^{13}$C SSNMR spectrum comprising peaks at 18.6, 164.5, and 171.8 ppm;
an FT-Raman spectrum comprising peaks at 748, 774, 1006, 1216, and 1717 cm$^{-1}$; and
a DSC endotherm with an onset at 119-120° C.

In another embodiment, Compound I, Form 7 is characterized by an XRPD spectrum comprising peaks at 12.6 and 13.5, and a $^{13}$C SSNMR spectrum comprising peaks at 18.6, 164.5, and 171.8 ppm. In another embodiment, Compound I, Form 7 is characterized by an XRPD spectrum comprising peaks at 12.6, 13.5, and 17.3, and a $^{13}$C SSNMR spectrum comprising peaks at 18.6, 164.5, and 171.8 ppm. In another embodiment, Compound I, Form 7 is characterized by an XRPD spectrum comprising peaks at 12.6, 13.5, 16.9, and 17.3 °2θ, and a $^{13}$C SSNMR spectrum comprising peaks at 18.6, 21.5, 68.7, 81.7, 102.8, 164.5, 151.4 and 171.8 ppm.

One embodiment is a process for making Compound I, Form 7, comprising contacting (S)-isopropyl 2-(((S)-(((2R, 3R,4R,5R)-5-(2,4-dioxo-3,4-dihydropyrimidin-1(2H)-yl)-4-fluoro-3-hydroxy-4-methyltetrahydrofuran-2-yl)methoxy) (phenoxy)phosphoryl)amino) propanoate with a solvent comprising isopropyl acetate and heptane, whereby Compound I, Form 7 is formed. In another embodiment, the solvent comprises THF. In another embodiment, the process further comprises seeding with a seed crystal of Compound I, Form 7. In another embodiment, the process further comprises isolating Compound I Form 7.

Another embodiment is crystalline (S)-isopropyl 2-(((S)-(((2R,3R,4R,5R)-5-(2,4-dioxo-3,4-dihydropyrimidin-1 (2H)-yl)-4-fluoro-3-hydroxy-4-methyltetrahydrofuran-2-yl) methoxy)(phenoxy)phosphoryl)amino) propanoate (Compound I, Form 8) characterized by an X-ray powder diffractogram comprising at least three of the following peaks chosen from the following list: 8.6, 9.2, 14.2, 15.6, 16.0, 17.1, 17.5, 18.1, 19.8, and 25.6 °2θ±0.2° 2θ. Another embodiment is crystalline Compound I, Form 8, characterized by an XRPD diffractogram comprising at least 5 peaks chosen from the following list: 8.6, 9.2, 14.2, 15.6, 16.0, 17.1, 17.5, 18.1, 19.8, and 25.6 °2θ±0.2° 2θ. Another embodiment is crystalline Compound I, Form 8, characterized by an XRPD diffractogram comprising peaks at 8.6, 9.2 and 17.1 °2θ±0.2° 2θ.

Figure 6:
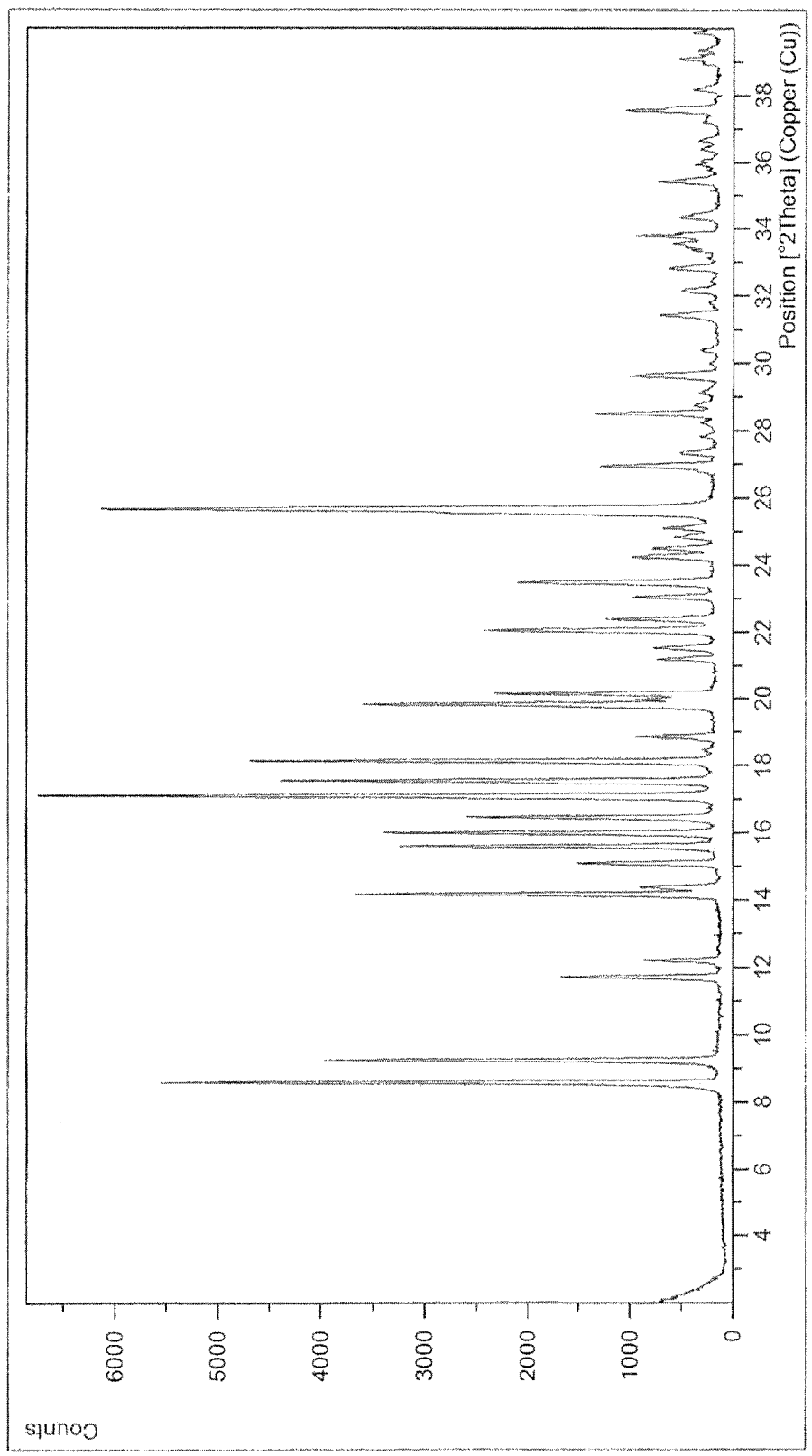
FIG. 6 is an XRPD diffractogram of Compound I, Form 8.

Another embodiment is crystalline Compound I, Form 8, characterized by an XRPD diffractogram comprising d-spacing values at 10.3, 9.6, and 5.2 angstroms (Å). In yet another embodiment, the crystalline Compound I, Form 8 has at least three of the following d-spacing: 10.3, 9.6, 6.3, 5.7, 5.5, 5.2, 5.1, 4.9, 4.5, and 3.5 angstroms (Å). In still another embodiment, the crystalline Compound I, Form 8 has at least five of the following d-spacing: 10.3, 9.6, 6.3, 5.7, 5.5, 5.2, 5.1, 4.9, 4.5, and 3.5 angstroms (Å). The relationship between peak positions and d-spacing values for Form 8 is found in Table 1. Another embodiment is crystalline Compound I, Form 8, characterized by an XRPD diffractogram having peak positions (2θ values) substantially as listed for Form 8 in Table 1. Another embodiment is crystalline Compound I, Form 8, characterized by an XRPD diffractogram having d-spacing values substantially as listed for Form 8 in Table 1. Another embodiment is crystalline Compound I, Form 8, characterized by an XRPD diffractogram substantially as shown in FIG. 6.

Figure 7:
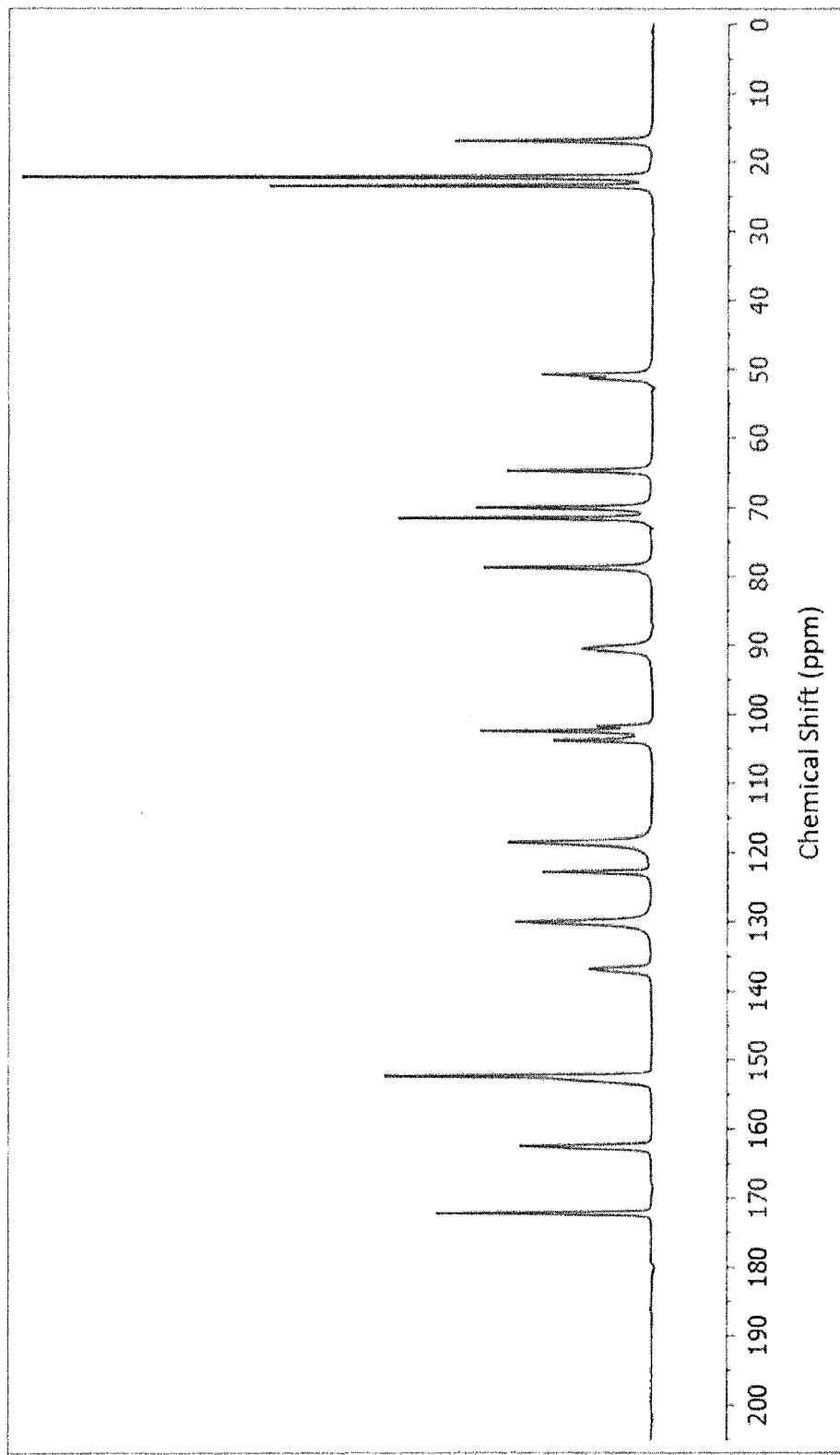
FIG. 7 is a $^{13}C$ SSNMR spectrum of Compound I, Form 8.

In another embodiment, Compound I, Form 8 is characterized by a $^{13}C$ SSNMR spectrum comprising peaks at 23.5, 70.1, and 152.4 ppm. In another embodiment, the $^{13}C$ SSNMR spectrum further comprises peaks at 22.2, 71.6, 78.8, 118.6 and 172.2 ppm. In another embodiment, Compound I, Form 8 is characterized by a $^{13}C$ solid state nuclear magnetic resonance spectrum substantially as shown in FIG. 7.

Figure 8:
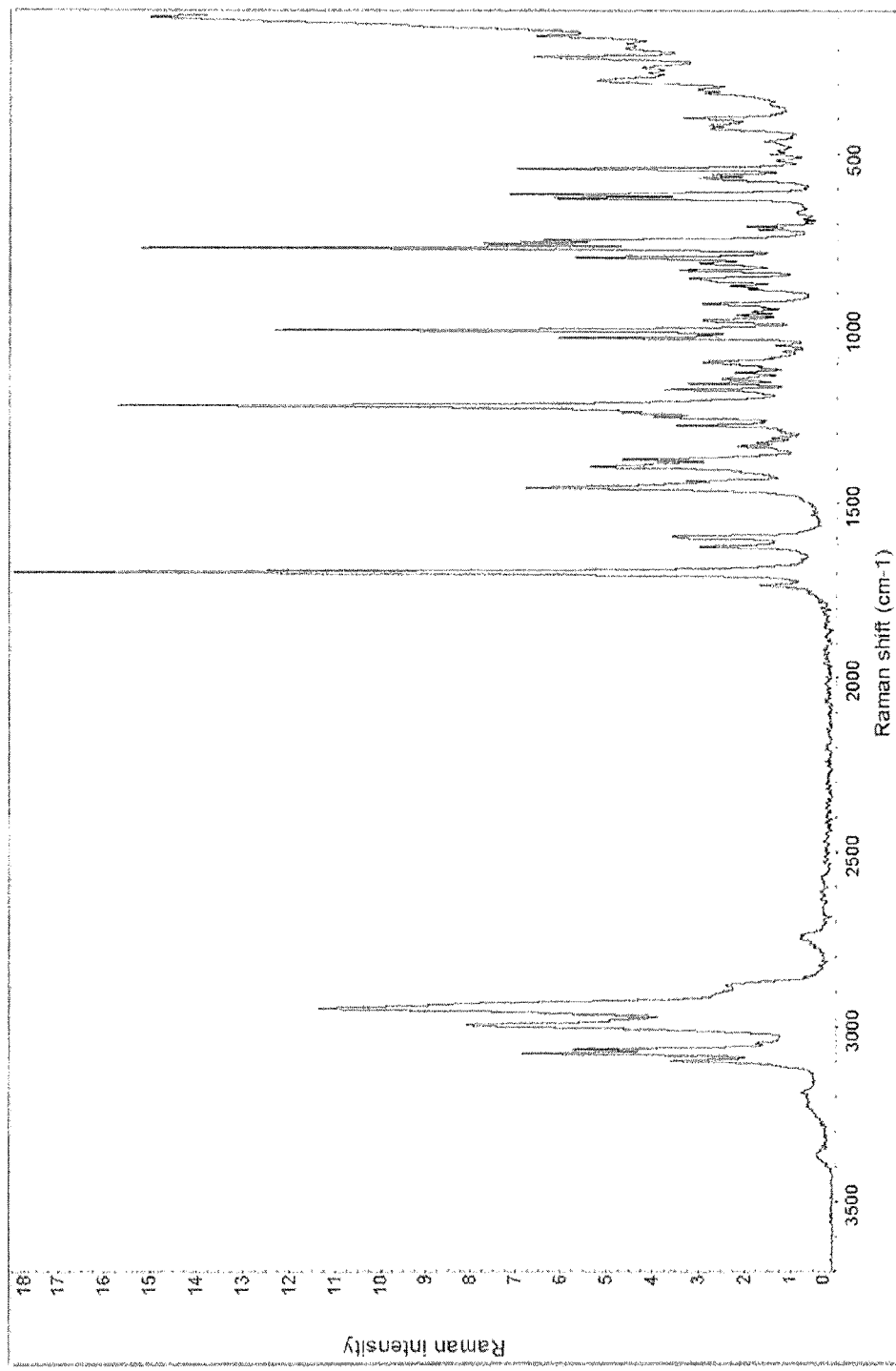
FIG. 8 is an FT-Raman spectrum of Compound I, Form 8.

In another embodiment, Compound I, Form 8 is characterized by an FT-Raman spectrum comprising peaks at 628, 759, 1029, 1224, and 1701 cm$^{-1}$. In another embodiment, the FT-Raman spectrum further comprises peaks at 221, 290, 543, 1397, 2994, and 3076 cm$^{-1}$. In another embodiment, Compound I, Form 8 is characterized by an FT-Raman spectrum substantially as shown in FIG. 8.

Figure 9:
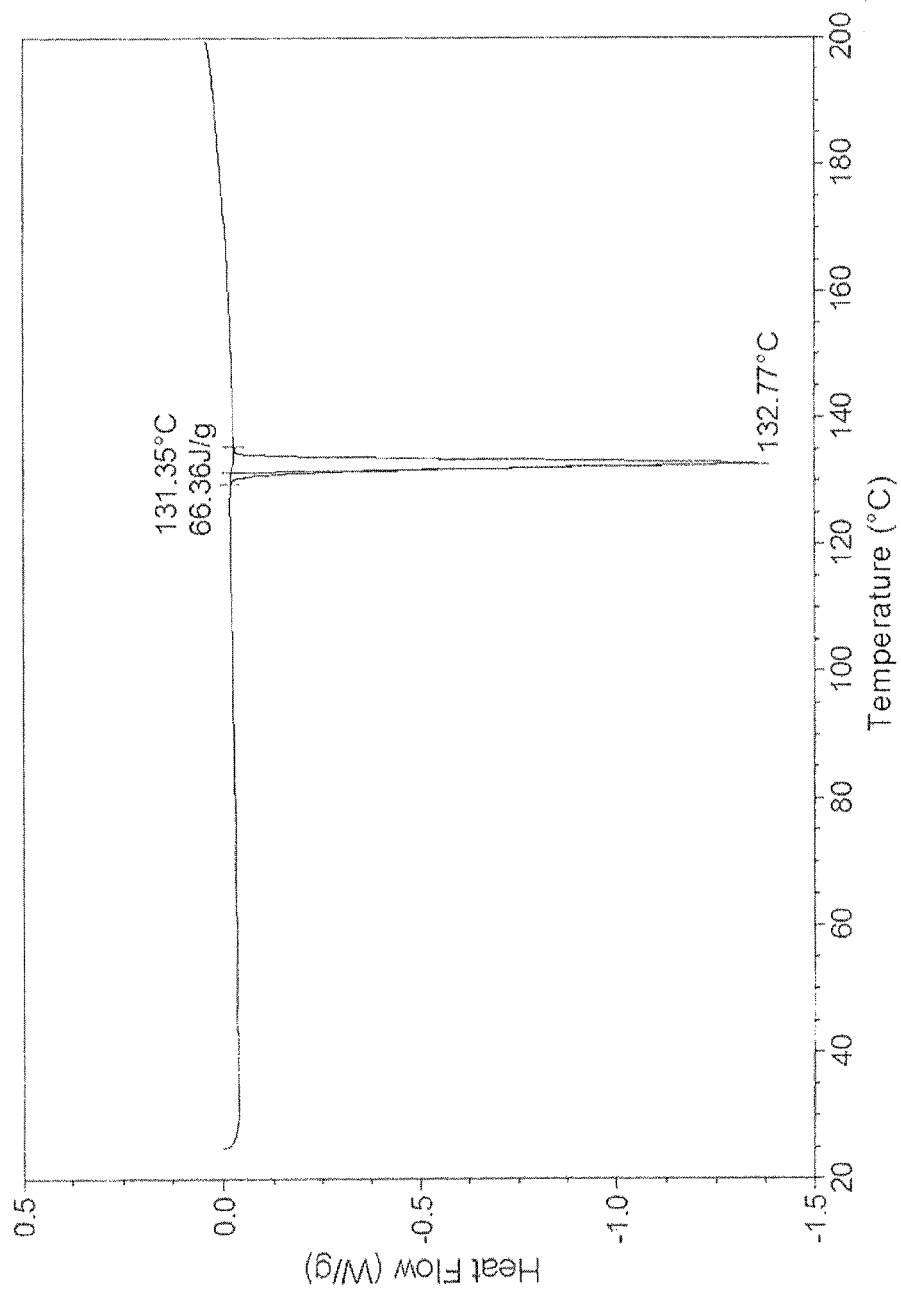
FIG. 9 is a DSC plot of Compound I, Form 8.

In another embodiment, Compound I, Form 8 is characterized by a differential scanning calorimetry (DSC) endotherm with an onset at 131-132° C. In another embodiment, Compound I, Form 8 is characterized by a DSC endotherm with a peak at about 133° C. In another embodiment, the DSC curve is substantially as shown in FIG. 9.

Figure 10:
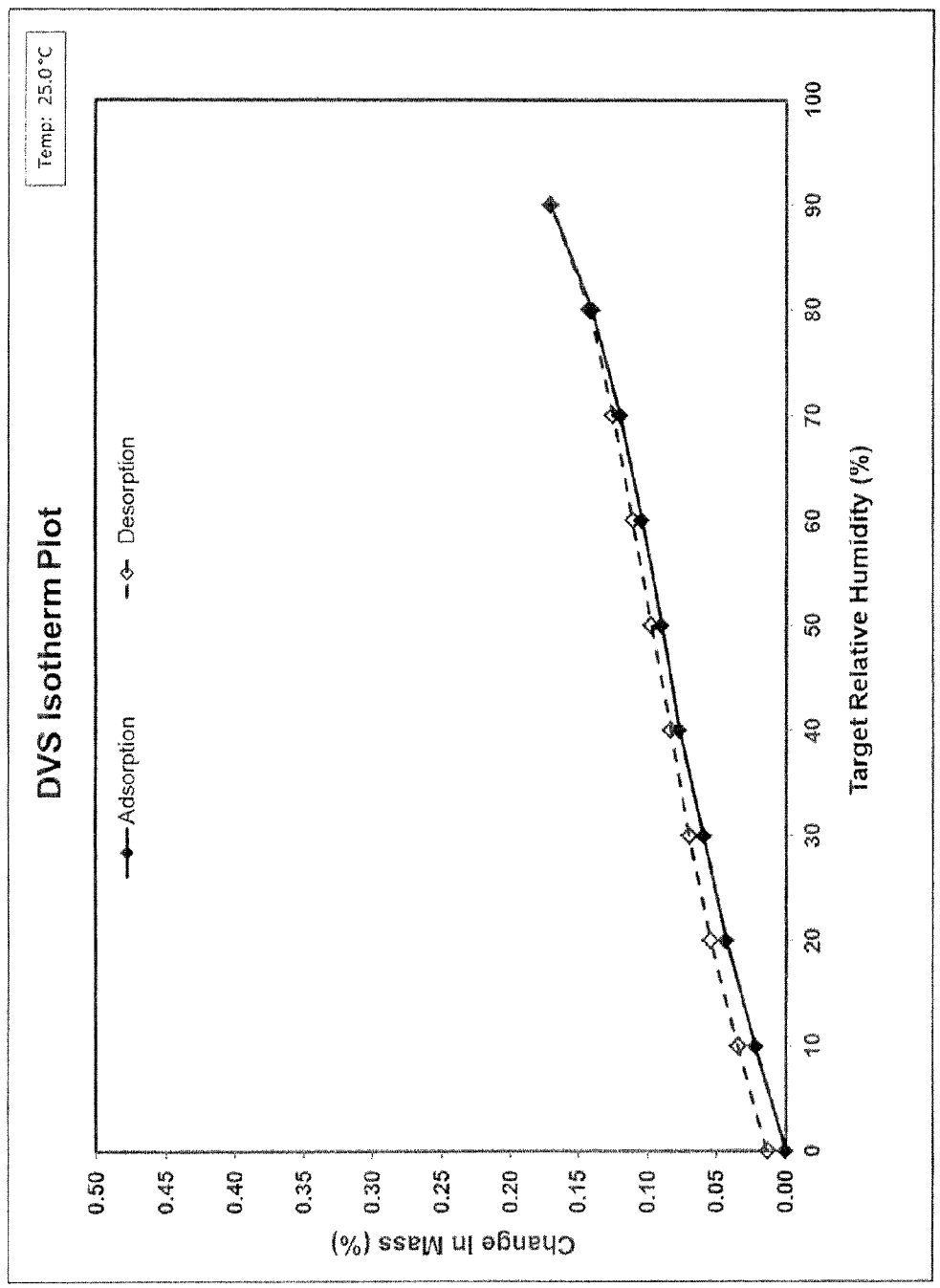
FIG. 10 is a DVS plot of Compound I, Form 8.

In another embodiment, Compound I, Form 8 is characterized by a change in mass of about 0.17% at a relative humidity of 90% relative humidity, (sorption cycle 1) as measured by dynamic vapor sorption (DVS). In another embodiment, the DVS is substantially as shown in FIG. 10.

In another embodiment, Compound I, Form 8 is characterized by at least two of the following:

an XRPD spectrum comprising peaks at 8.6, 9.2 and 17.1 °2θ;

a $^{13}C$ SSNMR spectrum comprising peaks at 23.5, 70.1, and 152.4 ppm;

an FT-Raman spectrum comprising peaks at 628, 759, 1029, 1224, and 1701 cm$^{-1}$; and a DSC endotherm with an onset at 131-132° C.

In another embodiment, Compound I, Form 8 is characterized by an XRPD spectrum comprising peaks at 8.6, 9.2 and 17.1 °2θ and a $^{13}C$ SSNMR spectrum comprising peaks at 23.5, 70.1, and 152.4 ppm. In another embodiment, Compound I, Form 8 is characterized by an XRPD spectrum comprising peaks at 8.6, 9.2 and 17.1 °2θ and a $^{13}C$ SSNMR spectrum comprising peaks at 22.2, 23.5, 70.1, 71.6, 78.8, 118.6, 152.4 and 172.2 ppm.

One embodiment is a process for making Compound I, Form 8, comprising contacting (S)-isopropyl 2-(((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino) propanoate with a solvent comprising isopropyl acetate, whereby Compound I, Form 8 is formed. In another embodiment, the process further comprises seeding with a seed crystal of Compound I, Form 8. In another embodiment, the process further comprises isolating Compound I, Form 8.

Forms 7 and 8 of Compound I provided in accordance with the present disclosure may be administered in the form of pharmaceutical compositions. This disclosure therefore provides pharmaceutical compositions that contain, as the active ingredient, one or more of Forms 7 and 8 of Compound I and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one embodiment, provided herein is a pharmaceutical composition comprising Compound I, Form 7 and a pharmaceutically acceptable carrier. In another embodiment, provided herein is a pharmaceutical composition comprising Compound I, Form 8 and a pharmaceutically acceptable carrier. In various embodiments, a pharmaceutical composition can comprise Compound I in more than one solid form. For example, a pharmaceutical composition can comprise Compound I, Form 7 at about 1 to about 100 percent (wt/wt) of the total amount of Compound 1. For example, a pharmaceutical composition can comprise Compound I, Form 7 at about 1 to about 40 percent of the total amount of Compound 1. For example, a pharmaceutical composition can comprise Compound I, Form 7 at about 1 to about 20 percent (i.e. about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent) of the total amount of Compound 1. By way of further example, a pharmaceutical composition can comprise Compound I, Form 8 at about 1 to about 100 percent (wt/wt) of the total amount of Compound 1. For example, a pharmaceutical composition can comprise Compound I, Form 8 at about 1 to about 40 percent of the total amount of Compound I. For example, a pharmaceutical composition can comprise Compound I, Form 8 at about 1 to about 20 percent (i.e. about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent) of the total amount of Compound 1.

Form 7 and Form 8 of Compound I may be administered orally or formulated for oral administration. Administration may be via capsule or enteric coated tablets or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include: lubricating agents such as talc, magnesium stearate and mineral oil; wetting agents; emulsifying and suspending agents; preserving agents such as methyl and propylhydroxy-benzoates; sweetening agents; and flavoring agents.

In some embodiments, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, each dosage unit contains from 1 mg to 2 g of a Compound I, Form 7 or Form 8, and for parenteral administration, in some embodiments, from 0.1 to 700 mg of Compound I, Form 7 or Form 8. In some embodiments, each dosage unit contains about 400 mg of Compound I, Form 7 or Form 8. It will be understood, however, that the amount of the compound actually administered usually will be determined by a physician, in the light of the relevant circumstances, including the condition to be treated, the chosen route of administration, the actual compound administered and its relative activity, the age, weight and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. In one embodiment, the film coating is a polyvinylalcohol-based coating.

In other embodiments, provided herein are pharmaceutical unit dosage forms comprising the pharmaceutical compositions provided herein. In some embodiments, the pharmaceutical unit dosage forms comprise from about 10 mg to about 1000 mg of Compound I, which may contain from about 1 to about 99 percent of Form 7 or Form 8. In various embodiments, the pharmaceutical dosage form comprises about 50, or about 100, or about 150, or about 200, or about 250, or about 300, or about 350, or about 400, or about 450, or about 500, or about 550, or about 600, or about 650, or about 700, or about 750, or about 800 mg of Compound I. In a further embodiment, the pharmaceutical dosage form comprises about 400 mg of Compound I. In one embodiment, a pharmaceutical dosage form comprises about 400 mg of Compound I, wherein the amount of Form 7 is from about 1 to about 100 percent of the total amount of Compound I. In one embodiment, a pharmaceutical dosage form comprises about 400 mg of Compound I, wherein the amount of Form 7 is from about 1 to about 40 percent of the total amount of Compound I. In one embodiment, a pharmaceutical dosage form comprises about 400 mg of Compound I, wherein the amount of Form 7 is from about 1 to about 20 percent (i.e. about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent) of the total amount of Compound I. In one embodiment, a pharmaceutical dosage form comprises about 400 mg of Compound I, wherein the amount of Form 8 is from about 1 to about 100 percent of the total amount of Compound I. In one embodiment, a pharmaceutical dosage form comprises about 400 mg of Compound I, wherein the amount of Form 8 is from about 1 to about 40 percent of the total amount of Compound I. In one embodiment, a pharmaceutical dosage form comprises about 400 mg of Compound I, wherein the amount of Form 8 is from about 1 to about 20 percent (i.e. about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent) of the total amount of Compound I.

Compound I, Form 7 or Form 8 described herein may be administered to a human subject suffering from hepatitis C virus (HCV) in either single or multiple doses by any of the accepted modes of administration known to those who are skilled in the art and as detailed above. In one embodiment, provided herein is a method of treating a human subject infected with hepatitis C virus comprising administering to the human subject a therapeutically effective amount of Compound I Form 7. In another embodiment, provided herein is a method of treating a human subject infected with hepatitis C virus comprising administering to the human subject a therapeutically effective amount of Compound I, Form 8. In another embodiment, provided herein is a method of treating a human subject infected with hepatitis C virus comprising administering to the human subject a pharmaceutical composition comprising a therapeutically effective amount of Compound I, Form 7 and a pharmaceutically acceptable carrier. In another embodiment, provided herein is a method of treating a human subject infected with hepatitis C virus comprising administering to the human subject a pharmaceutical composition comprising a therapeutically effective amount of Compound I, Form 8 and a pharmaceutically acceptable carrier. In still another embodiment, provided herein is a crystalline form of Compound I, Form 7 or a pharmaceutical composition comprising the crystalline form of Compound I, Form 7 and a pharmaceutically acceptable carrier for the treatment of a human subject infected by a hepatitis C virus. In yet another embodiment, provided herein is a crystalline form of Compound I, Form 8 or a pharmaceutical composition comprising the crystalline form of Compound I, Form 8 and a pharmaceutically acceptable carrier for the treatment of a human subject infected by a hepatitis C virus. In a further embodiment, provided herein is the use of a crystalline form of Compound I, Form 7 or a pharmaceutical composition comprising the crystalline form of Compound. I, Form 7 and a pharmaceutically acceptable carrier for the treatment of a human subject infected by a hepatitis C virus. In yet another embodiment, provided herein is the use of a crystalline form of Compound I, Form 8 or a pharmaceutical composition comprising the crystalline form of Compound I, Form 8 and a pharmaceutically acceptable carrier for the treatment of a human subject infected by a hepatitis C virus. In a further embodiment, provided herein is the use of a crystalline form of Compound I, Form 7 for the manufacture of a medicament for the treatment of a human subject infected by a hepatitis C virus. In yet another embodiment, provided herein is the use of a crystalline form of Compound I, Form 8 for the manufacture of a medicament for the treatment of a human subject infected by a hepatitis C virus.

In certain embodiments, pharmaceutical compositions, pharmaceutical dosage forms, and tablets comprising Compound I, Form 7 or Form 8, may be used in methods of treating one or more of genotype 1 HCV infected subjects (including genotypes 1a and 1b), genotype 2 HCV infected subjects, genotype 3 HCV infected subjects, genotype 4 HCV infected subjects, genotype 5 HCV infected subjects, and/or genotype 6 HCV infected subjects. Compound I, Form 7 or Form 8 may be used as a medicament. Compound I, Form 7 or Form 8 may be used for the treatment of hepatitis C. Compound I, Form 7 or Form 8 may be used in the manufacture of a medicament for the treatment of hepatitis C.

In certain methods, these pharmaceutical compositions, pharmaceutical dosage forms, or tablets may be administered to a subject in need thereof for about 24 weeks or less, about 22 weeks or less, about 20 weeks or less, about 18 weeks or less, about 16 weeks or less, about 12 weeks or less, about 10 weeks or less, about 8 weeks or less, or about 6 weeks or less or about 4 weeks or less.

Pharmaceutical compositions, pharmaceutical dosage forms, and tablets comprising Compound I, Form 7 or Form 8 may also comprise Compound I and another crystalline form. For example, certain pharmaceutical compositions, pharmaceutical dosage forms, and tablets comprising Compound I, Form 7 or Form 8 may also comprise Compound I, Form 6. In one embodiment, Compound I, Form 6 may be characterized by an X-ray powder diffractogram comprising peaks at about 6.1 and 12.7 °2θ. In another embodiment, Compound I, Form 6 may be characterized by an X-ray powder diffractogram comprising peaks at about 6.1, 8.2, 10.4, 12.7, 17.2, 17.7, 18.0, 18.8, 19.4, 19.8, 20.1, 20.8, 21.8 and 23.3 °2θ. In another embodiment, Compound I, Form 6 may be characterized by a differential scanning calorimetry (DSC) endotherm with an onset at 122-123° C. In another embodiment, Compound I, Form 6 is characterized by a DSC endotherm with a peak at about 125° C. U.S. Pat. No. 8,618,076, which is hereby incorporated herein by reference in its entirety, includes additional characterization information of Compound I, Form 6.

Human subjects being treated by administration of Compound I, Form 7 or Form 8 or both, described in the present disclosure may benefit from treatment with one or more additional anti-HCV agents. Such additional anti-HCV agents include interferons, ribavirin and its analogs, NS5A protease inhibitors, NS5B polymerase inhibitors, NS3 (NS3, NS3-NS4) protease inhibitors, alpha-glucosidase 1 inhibitors, hepatoprotectants, TLR-7 agonists, cyclophilin inhibitors, HCV IRES inhibitors, pharmacokinetic enhancers, and other anti-HCV agents. Combinations of these compounds can be selected based on the condition to be treated, cross-reactivities of ingredients and pharmaco-properties of the combination.

Examples of additional anti-HCV agents include, without limitation, the following:
A. interferons, for example, pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon affacon-1 (Infergen), interferon alpha-ni (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmuneribavirin and ribavirin analogs, e.g., rebetol, copegus, VX-497, and viramidine (taribavirin);
B. ribavirin and its analogs, for example, ribavirin (Rebetol, Copegus), and taribavirin (Viramidine);
C. NS5A inhibitors, for example, Compound A.1 (described below), Compound A.2 (described below), Compound A.3 (described below), ABT-267, Compound A.4 (described below), JNJ-47910382, daclatasvir (BMS-790052), ABT-267, Samatasvir, MK-8742, MK-8408, EDP-239, IDX-719, PPI-668, GSK-2336805, ACH-3102, A-831, A-689, AZD-2836 (A-831), AZD-7295 (A-689), and BMS-790052;
D. NS5B polymerase inhibitors, for example, Compound A.5 (described below), Compound A.6 (described below), ABT-333, Compound A.7 (described below), ABT-072, Compound A.8 (described below), tegobuvir (GS-9190), GS-9669, TMC647055, ABT-333, ABT-072, setrobuvir (ANA-598), IDX-21437, filibuvir (PF-868554), VX-222, IDX-375, IDX-184, IDX-102, BI-207127, valopicitabine (NM-283), PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A848837, GL59728, A-63890, A-48773, A-48547, BC-2329, BMS-791325, BILB-1941, and ACH-3422;
E. protease (NS3, NS3-NS4) inhibitors, for example, Compound A.9, Compound A.10, Compound A.11, ABT-450, Compound A.12 (described below), simeprevir (TMC-435), boceprevir (SCH-503034), narlaprevir (SCH-900518), vaniprevir (MK-7009), MK-5172, danoprevir (ITMN-191), sovaprevir (ACH-1625), neceprevir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061;

F. alpha-glucosidase 1 inhibitors, for example, celgosivir (MX-3253), Miglitol, and UT-231B;
G. hepatoprotectants, for example, emericasan (IDN-6556), ME-3738, GS-9450 (LB-84451), silibilin, and MitoQ;
H. TLR-7 agonists, for example, imiquimod, 852A, GS-9524, ANA-773, ANA-975, AZD-8848 (DSP-3025), and SM-360320;
I. cyclophillin inhibitors, for example, DEBIO-025, SCY-635, and NIM811;
J. HCV IRES inhibitors, for example, MCI-067;
K. pharmacokinetic enhancers, for example, BAS-100, SPI-452, PF-4194477, TMC-41629, GS-9350, GS-9585, and roxythromycin;
L. other anti-HCV agents, for example, thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, VX-497 (merimepodib) NIM811, benzimidazole derivatives, benzo-1,2,4-thiadiazine derivatives, and phenylalanine derivatives.

Compound A.1 is an inhibitor of the HCV NS5A protein and is represented by the following chemical structure:

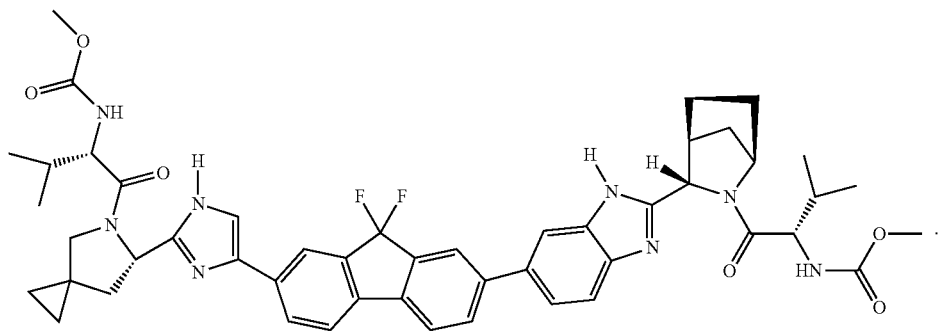

(see, e.g., U.S. Patent Application Pub. No. 20100310512 A1.).

Compound A.2 is an NS5A inhibitor and is represented by the following chemical structure:

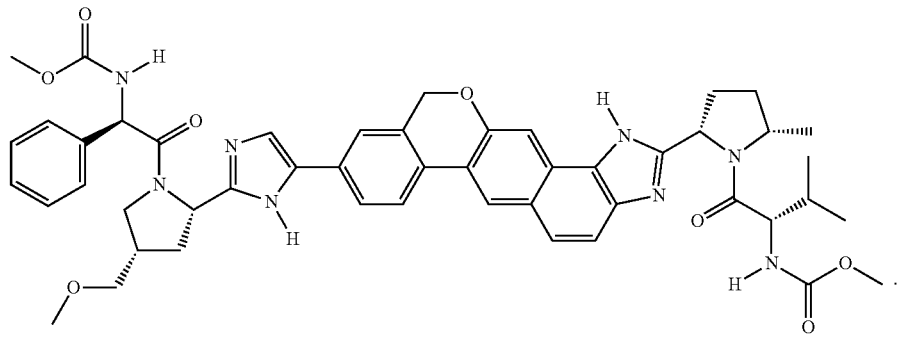 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

Compound A.3 is an NS5A inhibitor and is represented by the following chemical structure:

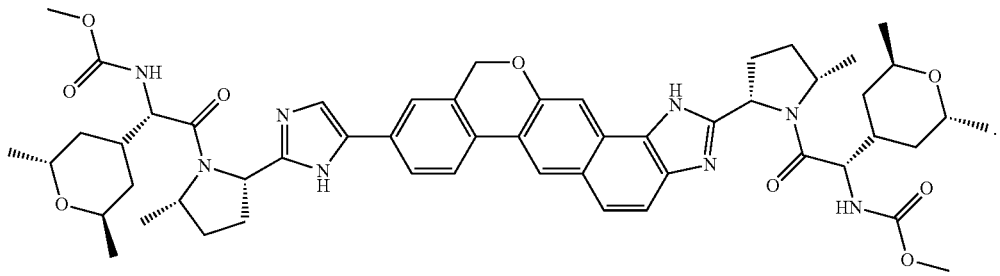

Compound A.4 is an NS5A inhibitor and is represented by the following chemical structure:

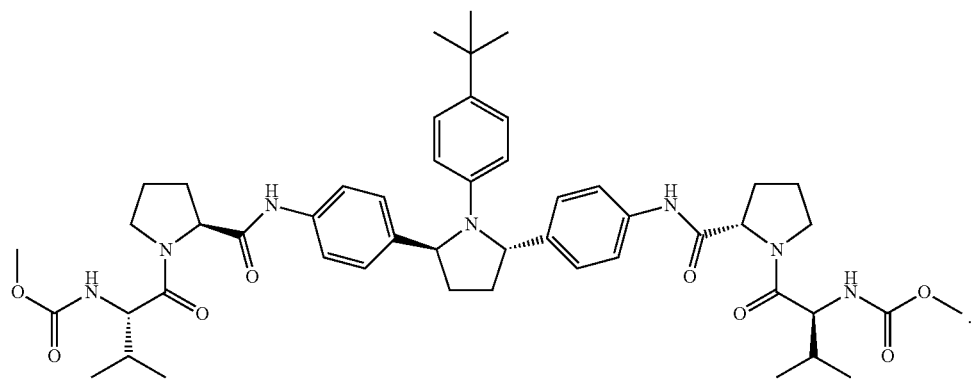 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)C)cc2)cc1)C(C)C]

See U.S. Publication No. 2013/0102525 and references therein.

Compound A.5 is an NS5B Thumb II polymerase inhibitor and is represented by the following chemical structure:

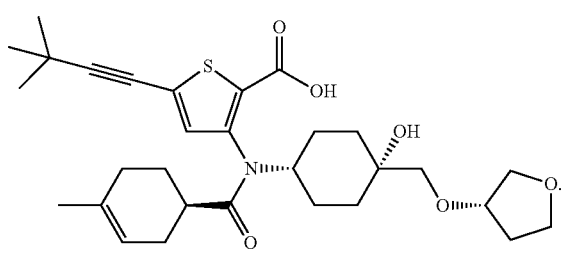 [SMILES: CC1=CC[C@H](C(=O)N(c2cc(C#CC(C)(C)C)sc2C(=O)O)[C@H]2CC[C@](O)(CO[C@H]3CCOC3)CC2)CC1]

Compound A.6 is a nucleotide inhibitor prodrug designed to inhibit replication of viral RNA by the HCV NS5B polymerase, and is represented by the following chemical structure:

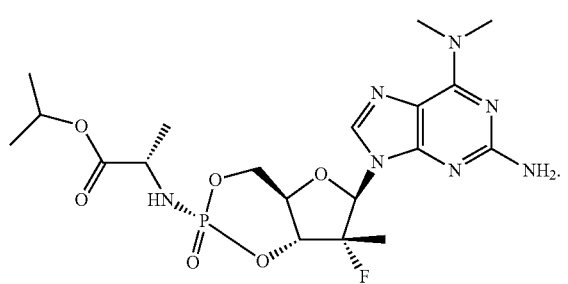 [SMILES: CC(C)OC(=O)[C@H](C)N[P@]1(=O)OC[C@H]2O[C@@H](n3cnc4c(N(C)C)nc(N)nc43)[C@](C)(F)[C@@H]2O1]

Compound A.7 is an HCV polymerase inhibitor and is represented by the following structure:

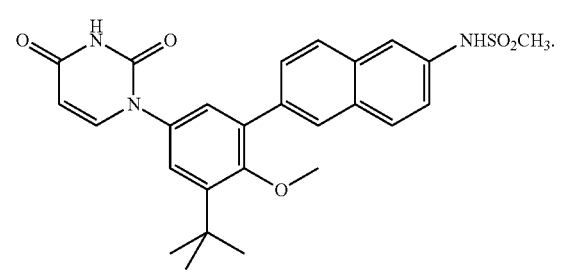

See U.S. Publication No. 2013/0102525 and references therein.

Compound A.8 is an HCV polymerase inhibitor and is represented by the following structure:

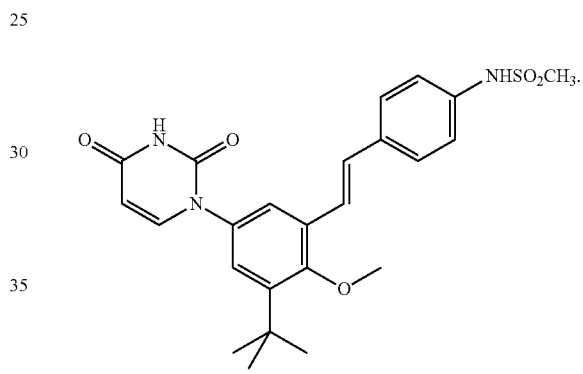

See U.S. Publication No. 2013/0102525 and references therein.

Compound A.9 is an HCV protease inhibitor and is represented by the following chemical structure:

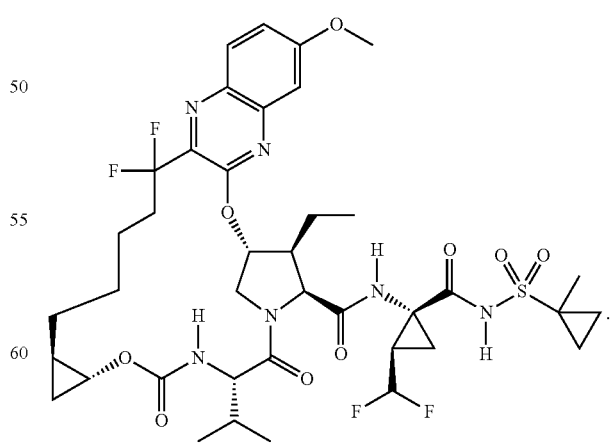

Compound A.10 is an HCV protease inhibitor and is represented by the following chemical structure:

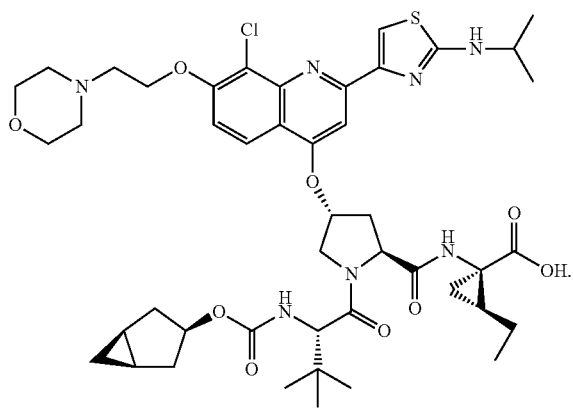

Compound A.11 is an HCV protease inhibitor and is represented by the following chemical structure:

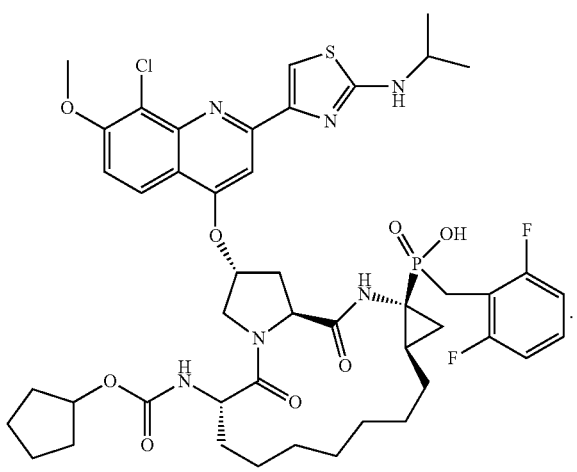 [SMILES: COc1ccc2c(O[C@@H]3C[C@H]4C(=O)N[C@]5(P(=O)(O)Cc6c(F)cccc6F)C[C@H]5CCCCCCC[C@H](NC(=O)OC5CCCC5)C(=O)N4C3)cc(-c3csc(NC(C)C)n3)nc2c1Cl]

Compound A.12 is an HCV protease inhibitor and is represented by the following chemical structure:

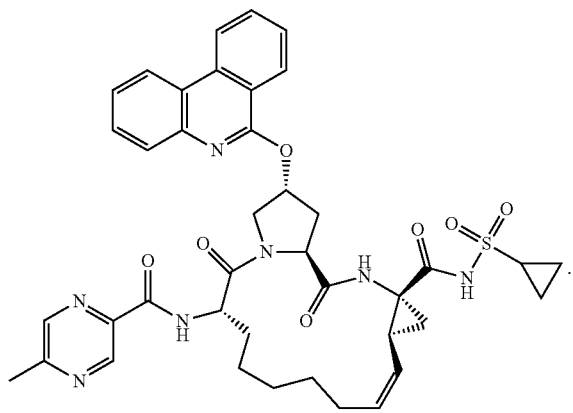 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccccc45)CN3C2=O)cn1]

See U.S. Publication No. 2013/0102525 and references therein.

In one embodiment, the additional anti-HCV agent is an HCV NS3 protease inhibitor. Non-limiting examples include the following:

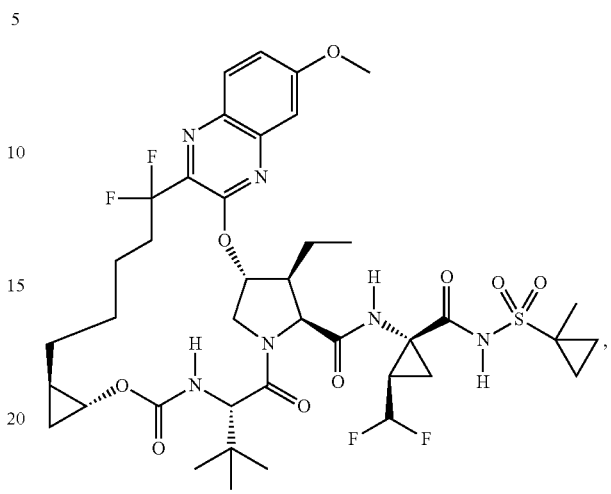

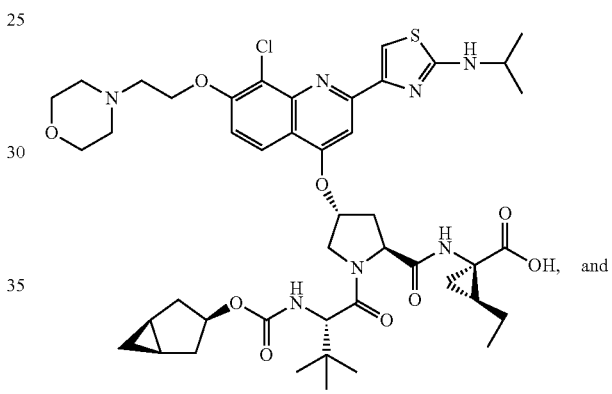

and

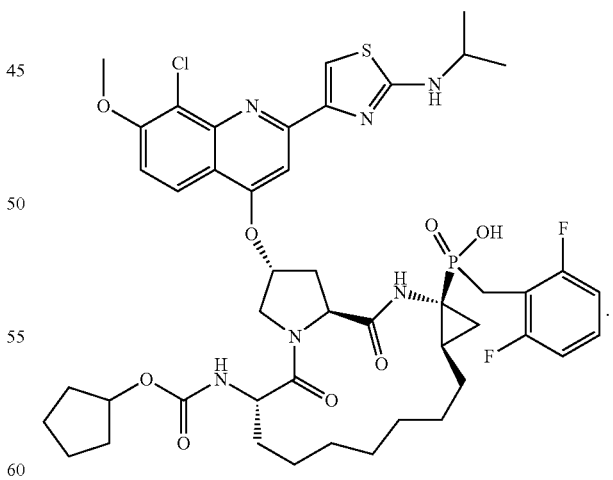

In another embodiment, the additional anti-HCV agent is a cyclophillin inhibitor, including for example, a cyclophilin inhibitor disclosed in WO2013/185093. Non-limiting examples in addition to those listed above include the following:

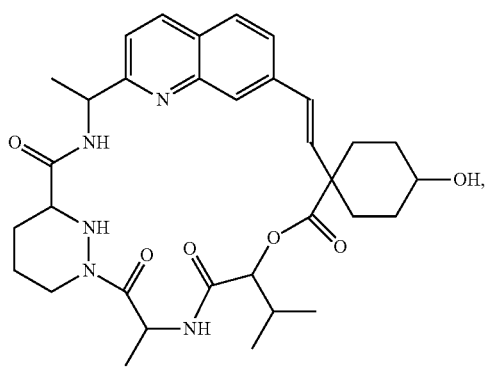
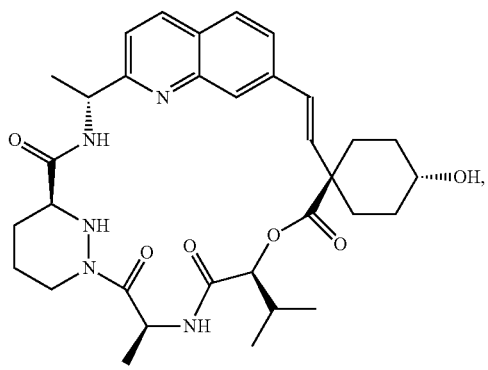
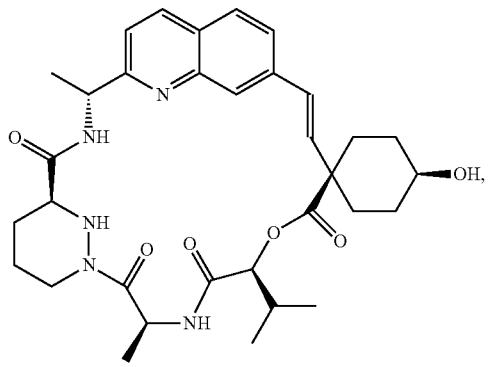
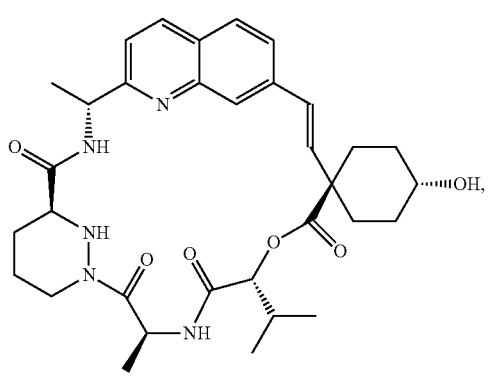
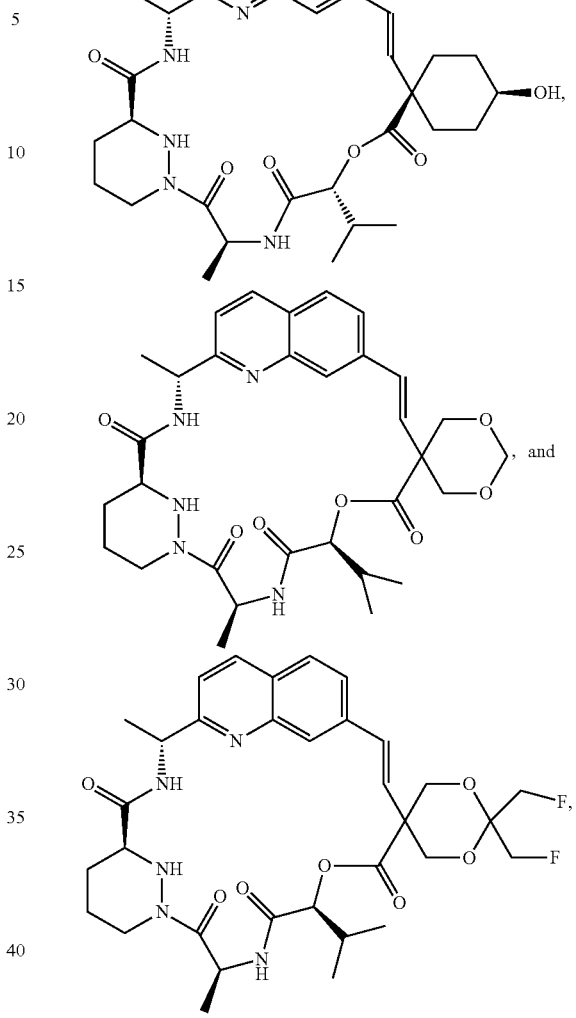

and stereoisomers and mixtures of stereoisomers thereof.

In one embodiment, the additional anti-HCV agent is MK-8742 or MK-8408. In one embodiment, the additional anti-HCV agent is MK-5172. In one embodiment, the additional anti-HCV agent is ABT-450, ABT-267, or ABT-333. In one embodiment, the additional anti-HCV agent is daclatasvir.

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms can be omitted from the drawn structures consistent with accepted shorthand notation of such organic compounds, and that one skilled in the art of organic chemistry would readily appreciate their presence.

X-ray diffraction was performed on a PANalytical X'Pert MPD Pro powder diffractometer equipped with an X'celerator detector. Data were acquired over the range of 2-40 °2θ, utilizing a step size of 0.017 °2θ and a step time of 50.165 seconds for a total analysis time of 15 minutes. Automatic divergence and anti-scatter slits were utilized. The instrument uses a copper anode, with the generator set to 40 mA and 45 kV during the analysis. The instrument was not equipped with an incident beam monochromator. All XRPD peak data herein expressed as degrees 2θ have an error of ±0.2° 2θ unless specified otherwise. Persons of ordinary skill in the art will know that errors in d-spacing values will vary depending on the corresponding peak position, and may be calculated using Bragg's Law.

Table 1 lists the ten most abundant XRPD peaks (° 2θ) for Compound I, Forms 7 and 8 and their corresponding d-spacing values (Å).

| Form 7 | | Form 8 | |
| --- | --- | --- | --- |
| Position (° 2θ) | d-Spacing (Å) | Position (° 2θ) | d-Spacing (Å) |
| 8.2 | 10.8 | 8.6 | 10.3 |
| 10.5 | 8.4 | 9.2 | 9.6 |
| 12.6 | 7.1 | 14.2 | 6.3 |
| 16.9 | 5.2 | 15.6 | 5.7 |
| 17.3 | 5.1 | 16.0 | 5.5 |
| 19.5 | 4.6 | 17.1 | 5.2 |
| 20.2 | 4.4 | 17.5 | 5.1 |
| 21.0 | 4.2 | 18.1 | 4.9 |
| 23.4 | 3.8 | 19.8 | 4.5 |
| 27.3 | 3.3 | 25.6 | 3.5 |

In the various embodiments described above, Compound I, Form 7 is characterized by XRPD diffractograms including peaks at 13.5 and 17.0 °2θ±0.2° 2θ, corresponding to d-spacing values of 6.6 and 5.2 angstroms, respectively.

Solid-state NMR ($^{13}$C SSNMR) spectra were conducted using an $^1$H-$^{13}$C cross-polarization magic angle spinning (CPMAS) experiment with total suppression of spinning sidebands (TOSS). Samples were packed into 7 mm $ZrO_2$ rotors analyzed with a Bruker Avance 400 MHz (1H frequency) NMR spectrometer. Spinning speeds of 4-5 kHz were used. All NMR peak data described herein is are expressed as ppm±0.2 ppm unless specified otherwise.

FT-Raman spectra were generated on a Thermo Scientific (Nicolet) Model 6700 FT-IR spectrophotometer coupled with a model NXR-9600 Raman module. The instrument utilizes a room-temperature InGaAs detector, and data were acquired from 3700-100 cm$^{-1}$. The data were acquired using a resolution of 4 cm$^{-1}$ and two levels of zero filling. All Raman peak data described herein are expressed as cm$^{-1}$±5 cm$^{-1}$ unless specified otherwise.

DSC thermograms were generated on a TA Instruments model Q2000 differential scanning calorimeter. Each sample was prepped in an individual "Tzero" aluminum hermetic sample pan. The samples were first equilibrated at 25° C., and then heated linearly at 2° C./minute to a final temperature of 200° C. The TA Instruments software is configured to represent exotherms in the "up" position and endotherms in the "down" position.

DVS isotherms were generated on a Surface Measurement Systems Dynamic Vapor Sorption Advantage moisture sorption analyzer. Water adsorption and desorption were studied as a function of relative humidity over the range of 0 to 90% RH using 10% RH steps with a fixed equilibration time of 60 minutes per step.

EXAMPLES

Example 1

Preparation of Compound I Form 7

The following procedure describes the preparation of Compound I, Form 7. Compound I was prepared as described in WO 2011/123645.

A solution of Compound I in THF/iPrOAc (tetrahydrofuran/isopropyl acetate) (about 2:1 w/w) was polish filtered, and the filtrate was distilled to a total volume of 5V. During distillation, the jacket temperature was maintained at or below 80° C. In a reactor, 10 V iPrOAc was added and the mixture was distilled to a total volume of about 5 V. The azeotrope was deemed complete when the THF content was not more than 4%. Then 7 V of iPrOAc was added. The temperature was adjusted to about 65° C., such as 60-70° C. Compound I was charged into the reactor and kept for 4 h until a slurry was formed. The slurry was cooled to about 20° C., such as 15-25° C., over at least 10 h and kept at about 20° C., such as 15-25° C., for at least 8 h. Then, 4.5 V n-heptane was added at an even rate over at least 1 h and the slurry was kept at about 20° C., such as 15-25° C. for at least 2 h. The contents of the reactor were filtered and the wet residue was rinsed with a mixture of 4 V iPrOAc and 1.3 V heptane. Volatiles were removed from the residue in vacuum oven at a temperature of no more than 40° C. until the loss on drying was less than 5%.

Example 2

Alternative Preparation of Compound I Form 7

Fifteen grams of Compound I in 6 vol IPA+6 vol heptane was heated to 60° C. to dissolve. The solution was cooled to 20° C. instantaneous by switching to a colder chiller. The cooled solution was seeded with Form 7 seed. Filtration was conducted after 3 h stirring at 20° C., obtained 0.5 g From 7 crystals. The filtrate was left in the hood and precipitated during ~16 h hold. Compound I, Form 7 was isolated from the filtrate Example 3

Preparation of Compound I, Form 8

Compound 1 was dissolved in 5 vol iPrOAc at 50° C., then seeded with 0.1% Form 8 seeds. A slurry of Form 8 was formed and was subsequently cooled to room temperature before filtration. The solids were dried at 35° C. in a vacuum oven.

Example 4

Alternative Preparation of Compound I, Form 8

A solution of Compound I in iPrOAc (20v/w) was heated to about 68° C. and stirred for 1 hour. After polish filtration, the filtrate was cooled down to about 40° C. and seed of Form 6 was added. The mixture was cooled down to about 20° C. without agitation. Once the crystals were formed, the solvent was decanted out and the crystals were collected.

While the foregoing description describes specific embodiments and aspects, those with ordinary skill in the art will appreciate that various modifications and alternatives can be developed. Accordingly, the particular embodiments and aspects described above are meant to be illustrative only, and not to limit the scope of the invention, which is to be given the full breadth of the appended claims, and any and all equivalents thereof.

What is claimed is:

1. A crystalline Compound I

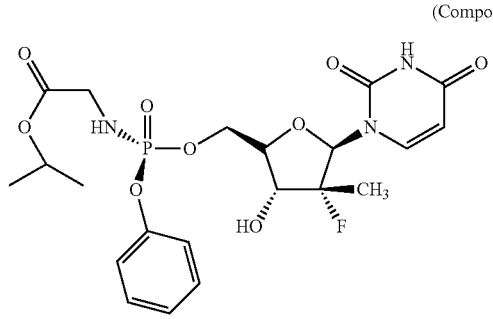
(Compound I)

characterized by an XRPD spectrum comprising peaks at 12.6 and 13.5 °2θ±0.2° 2θ.

2. The crystalline compound of claim 1, wherein the XRPD spectrum further comprises a peak at 17.3 °2θ±0.2° 2θ.

3. A crystalline Compound I

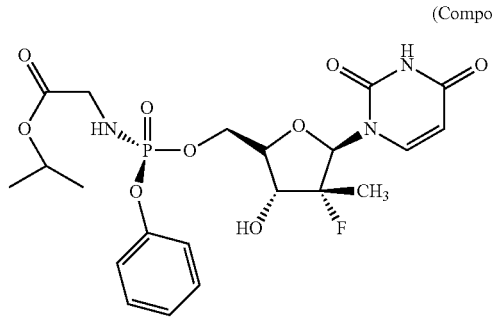
(Compound I)

characterized by a $^{13}$C SSNMR spectrum comprising peaks at 18.6, 164.5, and 171.8 ppm±0.2 ppm.

4. The crystalline compound of claim 3, wherein the $^{13}$C SSNMR spectrum further comprises peaks at 21.5, 68.7, 81.7, 102.8, and 151 ppm±0.2 ppm.

5. A crystalline Compound I:

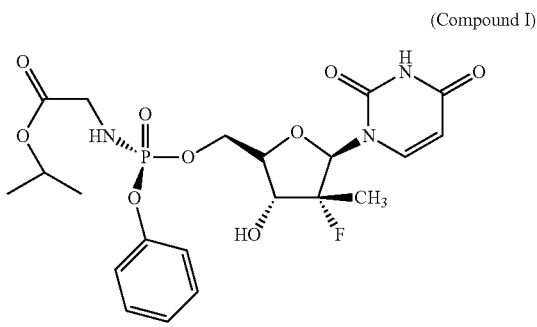
(Compound I)

characterized by an XRPD spectrum comprising peaks at 8.6, 9.2 and 17.1 °2θ±0.2° 2θ.

6. The crystalline compound of claim 5, wherein the XRPD spectrum further comprises peaks at 14.2, 15.6, 16.0, 17.5, 18.1, 19.8, and 25.6 °2θ±0.2° 2θ.

7. A crystalline Compound I:

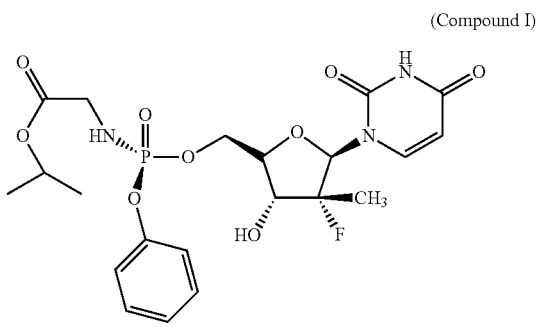
(Compound I)

characterized by a $^{13}$C SSNMR spectrum comprising peaks at 23.5, 70.1, and 152.4 ppm±0.2 ppm.

8. The crystalline compound of claim 7, wherein the $^{13}$C SSNMR spectrum further comprises peaks at 22.2, 71.6, 78.8, 118.6 and 172.2 ppm±0.2 ppm.

9. A pharmaceutical composition comprising the crystalline compound of claim 1 and a pharmaceutically acceptable excipient.

10. A method of treating a human subject infected with hepatitis C virus comprising administering to the human subject a therapeutically effective amount of the crystalline compound of claim 1.

* * * * *